United States Patent [19]

Plut et al.

[11] Patent Number: 4,899,357
[45] Date of Patent: Feb. 6, 1990

[54] X-RAY CONE SAFETY PLATE FOR X-RAY SYSTEM

[75] Inventors: Leonard F. Plut, Willowick; William F. Nyman, Newbury, both of Ohio

[73] Assignee: Picker International Inc., Highland Hts., Ohio

[21] Appl. No.: 242,150

[22] Filed: Sep. 9, 1988

[51] Int. Cl.⁴ .............................................. G21K 1/02
[52] U.S. Cl. ..................................... 378/148; 378/147
[58] Field of Search ................................ 378/148, 147

[56] References Cited

U.S. PATENT DOCUMENTS 2,998,526  8/1961  Green et al. ...................... 378/148

*Primary Examiner*—Craig E. Church
*Attorney, Agent, or Firm*—Fay, Sharpe, Beall, Fagan, Minnich & McKee

[57] ABSTRACT

An x-ray tube is enclosed in a housing 14, with a detachable x-ray cone 22 having an outward extending flange member 42, a cone holder 18 for receiving the flange member 42, a latch button 50 projecting from the holder for selectively releasing the cone 22 from the holder 18, and a safety plate assembly 26. The safety plate assembly is mounted between the cone holder and the housing 14 and has first and second tabs 28 which project from a periphery of a planar portion 30 of the safety plate substantially at right angles therewith. Each tab 28 has a projection 34 that is directed inward toward the other end generally at right angles with the tabs whereby a resting place is provided for the released cone 22 until the cone is manually removed.

15 Claims, 3 Drawing Sheets

X-RAY CONE SAFETY PLATE FOR X-RAY SYSTEM

BACKGROUND OF THE INVENTION

The present invention relates to the art of x-ray systems. It finds particular application in conjunction with x-ray systems having selectively removable, interchangeable x-ray cones and will be described with particular reference thereto. However, it is to be appreciated that the invention has broader application and may be advantageously employed in other environments.

Heretofore, typical x-ray systems that have provided for selectively removable, interchangeable x-ray cones also provided some sort of release mechanism, which, when activated, caused a particular cone that as received in the system to be released therefrom. Oftentimes, a button or latch projecting from an x-ray housing would be joined by a connecting member to a release mechanism located inside the system. Depression of the button or latch triggered the release mechanism, and the cone proceeded to fall from the system. If an operator or other person were not holding the cone, the cone would drop down and either injure a patient or damage the x-ray platform or cone. While injury to a patient is obviously a most undesirable result, broken x-ray platforms and bent cones are likewise undesirable because of the expense of replacement.

One of the problems with x-ray systems that have easily releasable cones is that, quite often, the operator leaves the room or turns away for a few moments while the portion of the patient to be examined is on the x-ray platform or table. Invariably, a curious patient may reach up toward the x-ray housing and depress the cone release button or latch. Not knowing that the cone must be held steady, the patient is injured as a result of the cone's having fallen from the system. Of course, a careless operator could also neglect to hold the cone upon activating the release mechanism, and will likewise cause the cone to fall upon and injure the patient.

Very little has been accomplished in attempting to provide safety features for the above-described x-ray system. One attempt, however, provided a protective piece or guard over the release button. Although the guard provided a temporary solution to the safety problem of inadvertently depressing the release button, it did not prevent the cone from falling once the button was depressed. Instead, the guard simply made the buttons more difficult to locate and depress.

In order to overcome the lack of safety features in x-ray systems having removable, interchangeable cones, it is desirable to develop a safety plate that is able to catch and retain a cone that is released from a system without injuring any patients or damaging the system. Further, it is desirable to develop a safety plate that would allow for the simple, fast manual removal of the cone.

The present invention contemplates a new and improved x-ray cone safety plate which overcomes the abovereferenced problems and others.

SUMMARY OF THE INVENTION

In accordance with the present invention, there is provided an x-ray cone safety plate for an x-ray system. The x-ray system includes removable, interchangeable cones which can be released or dropped from the system upon depressing a button or latch which activates a release mechanism inside the system. The safety plate catches the cone as it is released from the system.

In accordance with a more limited aspect of the invention, an x-ray system is provided. The x-ray system comprises an x-ray tube and a housing for enclosing the x-ray tube. A detachable x-ray cone having a first end and a second end includes a flange member extending outward along the outer perimeter of the first end. A holder for receiving the flange member is supported by the housing so that when the cone is in place and the system is operating, the cone's first end is situated above its second end, and radiation from the x-ray tube is directed through the cone. Further, a latch button projects from the holder for selectively releasing the cone from the holder. Finally, a safety plate assembly is mounted between the cone-holder and the housing, and has a pair of generally L-shaped tabs projecting downwardly therefrom, the tabs being disposed on opposite sides of the holder and extending partially under the holder whereby, upon releasing the cone with the latch button, the tabs catch the cone and prevent it from falling.

One advantage of the present invention is that it prevents a cone that is released from an x-ray system from falling and injuring a patient.

Another advantage of the present invention is that once a cone is caught by the safety plate, it can be manually removed therefrom by simple sliding movement.

Still further advantages of the present invention will become apparent to those of ordinary skill in the art upon a reading and understanding of the following detailed description of the preferred embodiment.

BRIEF DESCRIPTION OF THE DRAWINGS

The invention may take part in various parts and arrangement of parts. The drawings are only for purposes of illustrating a preferred embodiment and are not to be construed as limiting the invention.

DETAILED DESCRIPTION OF THE PREFERRED EMBODIMENT

Figure 1:
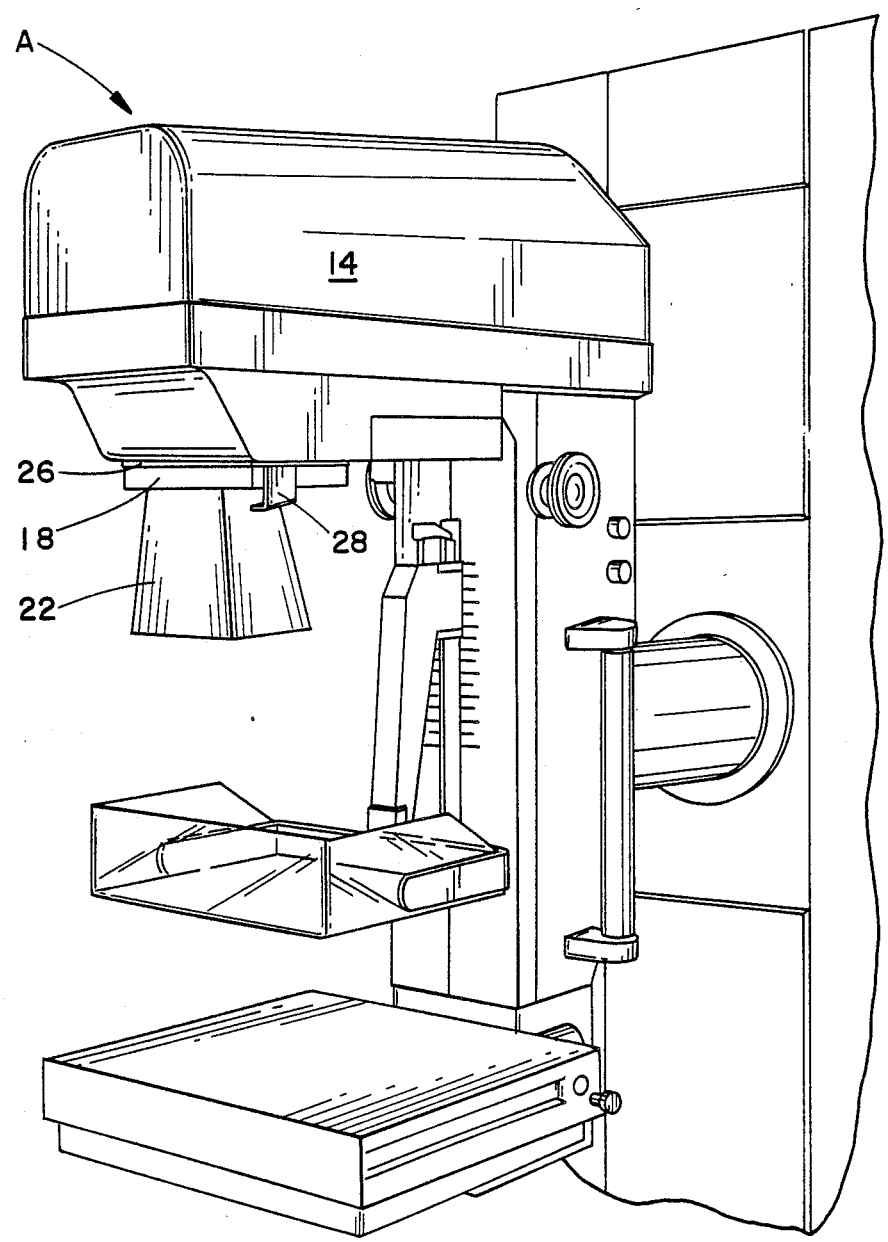
FIG. 1 is a perspective view of an x-ray system in accordance with the present invention.

With reference to FIG. 1, a radiographic apparatus or x-ray system A includes a housing 14 for enclosing the x-ray tube or other source of penetrating radiation. The housing 14 defines an opening therein for permitting penetrating radiation to pass downward therethrough. An x-ray cone holder 18 mounted adjacent the housing opening extends downward from, and is supported by, the housing 14. A detachable interchangeable x-ray cone 22 slides into place in holder 18 to shape and direct a beam of penetrating radiation. The system A provides for the applicability of various sizes of x-ray cones 22 to be placed into the cone holder 18.

Figure 2:
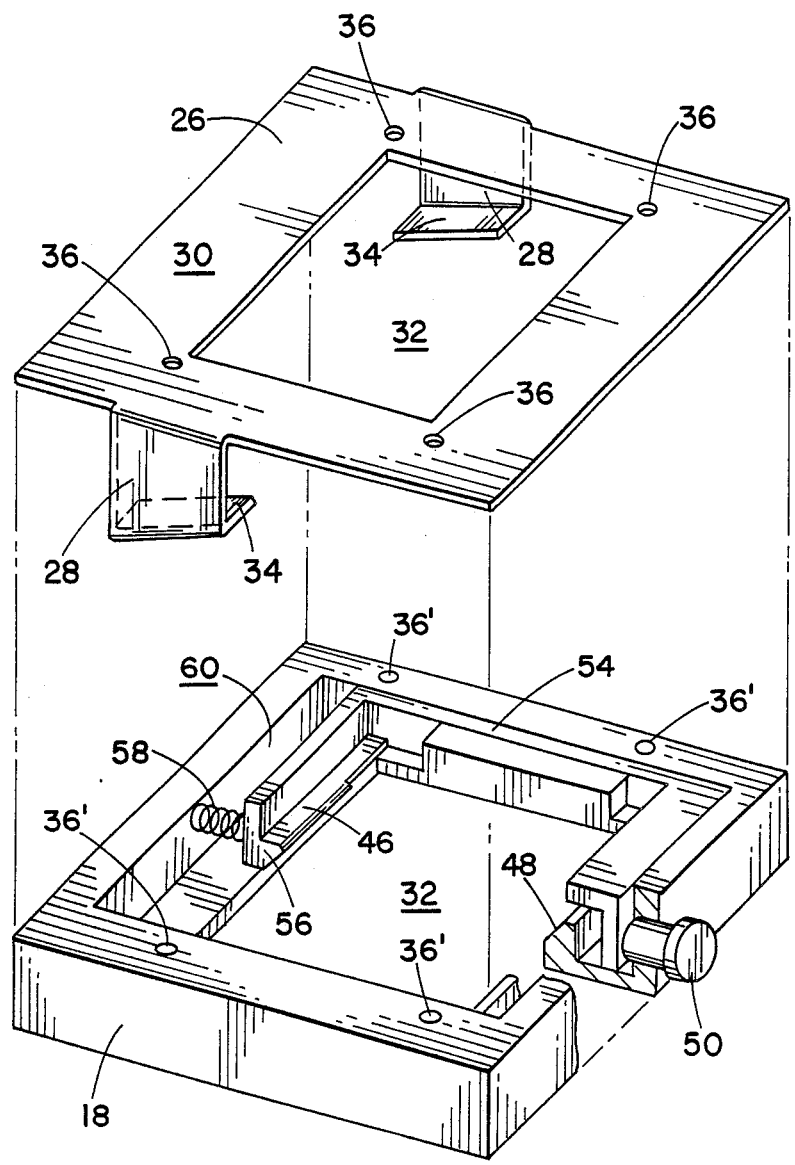
FIG. 2 is an exploded perspective view in partial section of an x-ray cone holder and a safety plate.

A safety means or safety plate assembly 26 is supported by the housing 14. In the preferred embodiment, the safety plate assembly is mounted between the housing 14 and the x-ray cone holder 18. It extends at least in part below holder 18. As is noted in FIG. 2, the safety plate 26 has first and second generally L-shaped tabs 28 projecting from a periphery of a generally planar portion 30 of the safety plate 26. The tabs 28 are disposed on opposite sides of the holder 18, and at general right angles with the planar portion 30.

The cone holder 18 defines an opening 32 into which the x-ray cone 22 is inserted. Formed of stamped metal or molded plastic, the safety plate 26 fits directly on the cone holder 18 with the planar portion 30 sitting flat on the holder, and the L-shaped tabs 28 extending below the level of the holder 18. First and second inward planar projections or supporting surfaces 34 of the tabs 28 extend inward toward the opening 32 and are disposed generally at right angles with the tabs. They do not, however, extend as far as the opening 32. The projections 34 are sloped or skewed relative to a horizontal plane. Their angle is slanted slightly upward toward the rear of the system A, with the lower portion being at the front. The slide surfaces of projections 34 are often covered with a material such as polytetrafluoroethylene for smooth sliding operation. Planar portion 30 defines a series of fastener-receiving holes 36 that are spaced along the periphery of opening 32. These holes 36 are aligned with like holes 36' in the holder 18 for fasteningly securing or clamping safety plate 26 and holder 18 to the system A with the existing mounting hardware for the holder.

Figure 3:
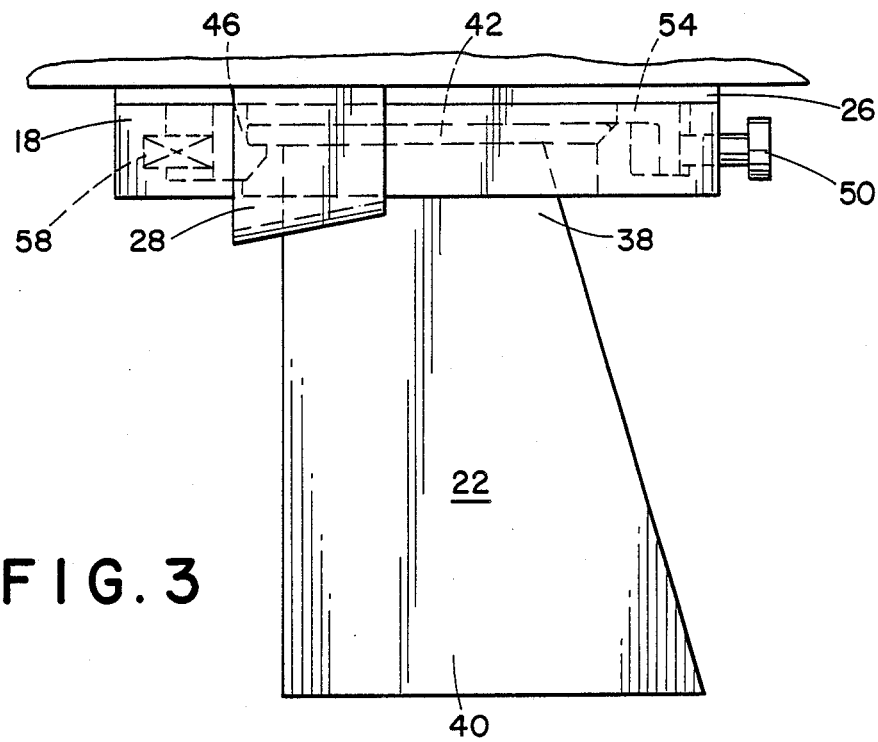
FIG. 3 is an elevational view of an x-ray cone, cone holder and safety plate, with broken lines showing how the x-ray cone fits on the cone holder.
Figure 4:
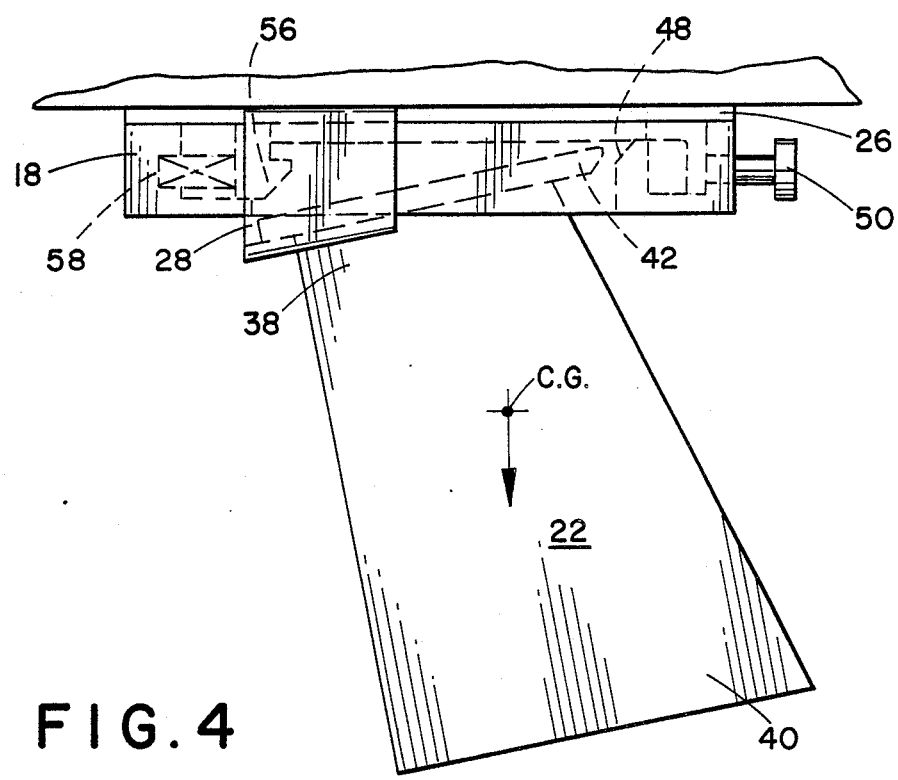
FIG. 4 is an elevational view of an x-ray cone that has been released from the cone holder and is resting on the safety plate, with broken lines showing how the x-ray cone rests on the safety plate.

As will be noted in FIGS. 3 and 4, the cone includes a first end 38 and a second end 40. A flange 42 extends outward along the outer perimeter of the first end 38 of the cone 22. One end of the flange 42 slides into a slot 46 of cone holder 18. The other end of the flange is inserted above a lip or ledge 48. When the cone 22 is properly inserted, sloped projections 34 of the safety plate 26 extend beneath the flange 42.

In order to remove the cone 22 from the holder 18, one selectively depresses a latch button 50 which extends outward of the holder 18. The latch button 50 is operatively joined by a connecting member 54 which follows along the perimeter of opening 32 to a release element 56 oppositely disposed from the latch button 50. A spring member 58 extends between an inner wall 60 of holder 18 and the release element 56 to bias the slot 46 toward the cone. FIG. 3 shows the cone 22 in place in holder 18 as it would be during the system A's operation. Spring member 58 is in a partially compressed state. Upon depression of latch button 50, the connecting member forces the release element 56 against the bias of spring member 58. When the spring member 58 is sufficiently compressed, the flange portion 42 falls from slot 46 and ledge 48. FIG. 4 shows the flange 42 released from the slot 46 and ledge 48, with the spring 58 in fully extended position.

When the latch button 50 is depressed, the flange 42 is released from slot 46 and drops downward to be captured by the L-shaped tabs 28. The flange 42 is then supported and engaged by the projections or supporting surface 34 of the safety plate 26. This can be seen most clearly in FIG. 4. The inward projections 34 of the L-shaped tabs 28 are sloped sufficiently so that the cone 22 does not drop downward but merely rests upon the inward projections 34. When the cone 22 is resting in place on the tabs 28, the cone does not rotate about the upper edge of tab extensions 34. The tabs are situated adjacent but displaced from the center of gravity of the released cone 22 such that the released cone tends to balance on the upper ends of the extensions. Gravity urges the released cone to tilt out of contact with the lower end of the extensions which inhibits free sliding movement along sloped surfaces 34. Interaction of the flange 42 and ledge 46 prevent the cone from being removed toward the upper end of the extensions. The center of gravity of the released cone 22 urges the released cone to rest on the extensions 34, and the extensions 34 prevent the released cone from falling. In order to remove the cone 22 from the system, an operator manually slides the cone along sloped extensions 34 to remove it from the lower end of projection 34 of the safety plate 26 and its tabs 28.

The invention has been described with reference to the preferred embodiment. Obviously, modifications and alterations will occur to others upon reading and understanding the preceding specification. It is intended that the invention be construed as including all such alterations and modifications insofar as they come within the scope of the appended claims or the equivalents thereof.

Having thus described the preferred embodiments, the invention is now claimed to be:

1. An x-ray system comprising:
   an x-ray tube;
   a housing for enclosing the x-ray tube;
   a detachable x-ray cone having a first end and a second end, the first end having a flange member extending outward along its outer perimeter;
   a holder for receiving the flange member, the holder being supported by the housing such that when the cone is in place and the system is operating, the cone's first end is situated above its second end and radiation from the x-ray tube is directed through the cone;
   a latch button projecting from the holder for selectively releasing the cone from the holder; and,
   a safety assembly depending downward below the housing, the safety assembly having first and second stationary tabs fixedly projecting therefrom, the tabs being disposed on opposite sides of the holder and extending partially under the cone flange member for catching the cone after it is released by the latch button.

2. A safety plate for catching a flanged x-ray cone which is released from a cone-holding component of an x-ray system, the safety plate comprising:
   a generally planar portion receivable between the cone-holding component and the housing;
   first and second stationary tabs projecting from a periphery of the planar portion substantially at right angles therewith, each tab having a shelf-like extension directed inward toward the other and extending at least partially under and displaced from a flange position of a held cone such that upon selective release of the cone from the cone-holding component, the flange portion of the cone drops onto and is supported by the shelf-like extensions, the extensions providing a resting place for the released cone until the released cone is removed from the shelf-like extensions.

3. The safety plate as set forth in claim 2 wherein the tab extensions are angled.

4. The safety plate as set forth in claim 2 wherein the extensions lie in a plane that is skewed relative the planar portion.

5. The safety plate as set forth in claim 2 wherein the safety plate is formed from stamped metal.

6. The safety plate as set forth in claim 2 wherein the safety plate is molded plastic.

7. A cone-release assembly for selectively releasing an x-ray cone which has an outward extending flange from an x-ray system, the cone-release assembly comprising:
   a housing;
   an x-ray cone holder for holding the x-ray cone;
   a latch for selectively releasing the cone from the holder;
   at least two stationary tabs projecting downward from adjacent opposite peripheral edges of the holder, the tabs each having an inward directed extension for supporting a first portion the x-ray cone after it is selectively released from the holder with a second portion of the cone abutting against the housing.

8. The cone-release assembly as set forth in claim 7 wherein the holder has a ledge for supporting the flange of the cone and the latch includes means for moving the ledge out of supporting alignment with the flange.

9. The cone release assembly as set forth in claim 7 wherein the tab extensions include sloped generally planar surfaces.

10. The cone release assembly as set forth in claim 9 wherein the tab extensions are situated adjacent to but offset from a center of gravity of the released cone such that gravity urges the released cone to tilt to inhibit free sliding movement along the sloped extensions.

11. A radiographic apparatus comprising:
   a housing having a source of penetrating radiation disposed therein, the housing defining an opening for permitting the penetrating radiation to pass downward therethrough;
   a cone holder mounted adjacent the housing opening for selectively mounting one of a plurality of radiation beam defining cones across the housing opening to shape and direct a beam of the penetrating radiation; and,
   a safety means supported by the housing and extending at least in part below the holder for catching a cone released from the holder, the safety means defining first and second generally parallel supporting surfaces which slope from an upper end to a lower end, whereby sliding removal of the released cone from the lower end is facilitated.

12. The apparatus as set forth in claim 11 wherein the safety means includes a pair of L-shaped tabs that extend downward from the holder and define the supporting surfaces thereon.

13. The apparatus as set forth in claim 12 wherein the safety means further includes a plate that defines an opening therein, the plate being mounted to at least one of the holder and the housing with the plate opening being aligned with the housing opening, the L-shaped tabs being operatively connected with the plate.

14. The apparatus as set forth in claim 11 wherein the supporting surface upper end is disposed off center from a center of gravity of the released cone such that gravity urges the released cone to tip, inhibiting free sliding movement along the supporting surface.

15. A method of safely removing an x-ray cone from an x-ray system, the method comprising:
   providing an x-ray system having at least an x-ray tube, a housing, a flange-bearing x-ray cone, an x-ray cone holder, a release element, and a safety plate;
   inserting the x-ray cone flange into the cone holder;
   depressing a latch button to cause the release element to move from supporting the flange whereby the cone is released and the cone drops;
   catching the dropped cone on stationary tabs which extend from the safety plate; and
   removing the cone from the system by horizontally sliding its flange along the tabs.

* * * * *